United States Patent
Sogard

(10) Patent No.: US 7,426,014 B2
(45) Date of Patent: Sep. 16, 2008

(54) DYNAMIC FLUID CONTROL SYSTEM FOR IMMERSION LITHOGRAPHY

(75) Inventor: Michael Sogard, Menlo Park, CA (US)

(73) Assignee: Nikon Corporation, Tokyo (JP)

( * ) Notice: Subject to any disclaimer, the term of this patent is extended or adjusted under 35 U.S.C. 154(b) by 0 days.

(21) Appl. No.: 11/628,960

(22) PCT Filed: May 18, 2005

(86) PCT No.: PCT/US2005/017161

§ 371 (c)(1),
(2), (4) Date: Dec. 8, 2006

(87) PCT Pub. No.: WO2006/007111

PCT Pub. Date: Jan. 19, 2006

(65) Prior Publication Data

US 2007/0177118 A1    Aug. 2, 2007

Related U.S. Application Data

(60) Provisional application No. 60/584,543, filed on Jul. 1, 2004.

(51) Int. Cl.
*G03B 27/42* (2006.01)
*G03B 27/52* (2006.01)

(52) U.S. Cl. .......................... 355/53; 355/30

(58) Field of Classification Search ............ 355/18, 355/53, 55, 30, 72; 430/396; 250/492.2, 250/492.21; 73/204.26, 54.09
See application file for complete search history.

(56) References Cited

U.S. PATENT DOCUMENTS

| | | | |
|---|---|---|---|
| 5,296,891 A | 3/1994 | Vogt et al. | |
| 5,523,193 A | 6/1996 | Nelson | |
| 2002/0020821 A1 | 2/2002 | Van Santen et al. | |
| 2003/0010096 A1* | 1/2003 | Long | 73/54.09 |
| 2004/0114117 A1 | 6/2004 | Bleeker | |
| 2005/0007569 A1 | 1/2005 | Streefkerk et al. | |
| 2005/0018156 A1 | 1/2005 | Mulkens et al. | |
| 2005/0030498 A1 | 2/2005 | Mulkens | |
| 2005/0174550 A1 | 8/2005 | Streefkerk et al. | |
| 2005/0178195 A1* | 8/2005 | Pinter et al. | 73/204.26 |

(Continued)

FOREIGN PATENT DOCUMENTS

EP    1 703 548 A1    9/2006

(Continued)

*Primary Examiner*—Peter B Kim
(74) *Attorney, Agent, or Firm*—Oliff & Berridge, PLC

(57) ABSTRACT

A dynamic fluid control system and method capable of reducing dynamic forces from the fluid on the last optical element (20) and substrate stage (14) caused by the motion of the immersion fluid. The system includes an imaging element (12) that defines an image and a stage (14) configured to support a substrate (16). An optical system (18) is provided to project the image defined by the imaging element onto the substrate. The optical system (18) includes a last optical element (20). A gap (22) filled with immersion fluid is provided between the substrate (16) and the last optical element (20). A dynamic force control system (34) is provided to maintain a substantially constant force on the last optical element and the stage (14) by compensating for dynamic changes of the immersion fluid caused by the motion of the immersion fluid through the gap and/or movement of the stage.

29 Claims, 9 Drawing Sheets

U.S. PATENT DOCUMENTS

| | | |
|---|---|---|
| 2005/0219481 A1 | 10/2005 | Cox et al. |
| 2005/0259233 A1 | 11/2005 | Streefkerk et al. |
| 2005/0259234 A1 | 11/2005 | Hirukawa et al. |
| 2005/0270506 A1 | 12/2005 | Streefkerk et al. |
| 2006/0097193 A1* | 5/2006 | Horsky et al. .......... 250/492.21 |
| 2006/0114445 A1 | 6/2006 | Ebihara |
| 2006/0126045 A1 | 6/2006 | Ono et al. |
| 2006/0139613 A1 | 6/2006 | Houkes et al. |
| 2006/0209278 A1 | 9/2006 | Kiuchi et al. |
| 2007/0081136 A1 | 4/2007 | Hara |

FOREIGN PATENT DOCUMENTS

| | | |
|---|---|---|
| JP | A-59-19912 | 2/1984 |
| WO | WO 98/33096 | 7/1998 |
| WO | WO 98/38597 | 9/1998 |
| WO | WO 2004/053955 A1 | 6/2004 |
| WO | WO 2004/090634 A2 | 10/2004 |
| WO | WO 2004/114380 A1 | 12/2004 |
| WO | WO 2005/006416 A1 | 1/2005 |
| WO | WO 2005/006417 A1 | 1/2005 |
| WO | WO 2005/024517 A2 | 3/2005 |
| WO | WO 2005/067013 A1 | 7/2005 |
| WO | WO 2005/093791 A1 | 10/2005 |

* cited by examiner

DYNAMIC FLUID CONTROL SYSTEM FOR IMMERSION LITHOGRAPHY

RELATED APPLICATIONS

This application claims priority on Provisional Application Ser. No. 60/584,543 filed on Jul. 1, 2004 and entitled "Fluid Control System for Immersion Lithography Tool". The contents of Provisional Application Ser. No. 60/584,543 are incorporated herein by reference for all purposes.

BACKGROUND

1. Field of the Invention

The present invention relates to immersion lithography, and more particularly, to a dynamic fluid control system and method capable of compensating for dynamic changes in the forces exerted on the last optical element and stage by the immersion fluid caused by the motion of the immersion fluid and movements of the stage.

2. Related Art

A typical lithography machine includes a radiation source, an imaging element defining an image pattern, an optical system, and a wafer stage to support and move the wafer. A radiation-sensitive material, such as resist, is coated onto the wafer surface prior to placement onto the wafer table. During operation, radiation energy from the radiation source is used to project the image pattern defined by the imaging element through the optical system onto the wafer. The optical system typically includes a number of lenses. The lens or optical element closest to the wafer is sometimes referred to as the "last" or "final" optical element.

The projection area during an exposure is typically much smaller than the wafer. The wafer therefore has to be moved relative to the optical system to pattern the entire surface. In the semiconductor industry, two types of lithography machines are commonly used. With so-called "step and repeat" machines, the entire image pattern is projected at once in a single exposure onto a target area of the wafer. After the exposure, the wafer is moved or "stepped" in the x and/or y direction and a new target area is exposed. This step and repeat process is performed over and over until the entire wafer surface is exposed. With scanning type lithography machines, the target area is exposed in a continuous or "scanning" motion. The patterning element is moved in one direction while the wafer is moved in either the same or the opposite direction during exposure. The wafer is then moved in the x and y direction to the next scan target area. This process is repeated until all the desired areas on the wafer have been exposed.

Immersion lithography systems use a layer of fluid that fills the gap between the final optical element of the optical assembly and the wafer. The fluid enhances the resolution of the system by enabling exposures with numerical apertures (NA) greater than one, which is the theoretical limit for conventional "dry" lithography. The fluid in the gap permits the exposure with radiation that would otherwise be completely internally reflected at the optical-air interface. With immersion lithography, numerical apertures as high as the index of refraction of the fluid are possible. Immersion also increases the depth of focus for a given NA, which is the tolerable error in the vertical position of the wafer, compared to a conventional lithography system. Immersion lithography thus has the ability to provide resolution down to 50 nanometers or lower.

In immersion systems, the fluid essentially becomes part of the optical system of the lithography tool. The optical properties of the fluid therefore must be carefully controlled. The optical properties of the fluid are influenced by the composition of the fluid, temperature, the absence or presence of gas bubbles, and out-gassing from the resist on the wafer.

The pressure and forces exerted by the immersion fluid on the last optical element and wafer stage should be constant. This desired result, however, is very difficult to achieve for a number of reasons.

With immersion lithography, the fluid is constantly removed and replenished. The removal of the fluid helps recover any contaminants and heat generated during exposure. Ideally, the amount of fluid being supplied should equal the amount being removed. A precise equilibrium, however, is difficult to achieve in practice. An uneven flow rate, which may result in a varying volume of fluid under the last optical element, may cause the forces and pressures acting on the last optical element and wafer stage to be dynamic.

The movement of the wafer stage also creates dynamic forces on the last optical element due to the behavior of the immersion fluid. For example, when the wafer stage starts accelerating, the shape of the fluid at the fluid-air interface, sometimes called the meniscus, changes. The meniscus tends to extend outward at the leading edge and pull-in at the trailing edge of the movement. The change in the shape in the meniscus creates a change in the static pressure exerted on the last optical element and stage by the immersion fluid.

The motion of the stage also creates waves in the immersion fluid. These waves may cause the last optical element to oscillate up and down as well as perturb the wafer stage. If the oscillations are still occurring during an exposure due to the lingering effects of the waves, the accuracy and image quality may be adversely affected.

Vertical adjustments of the wafer may also cause the volume of the gap between the last optical element and the wafer to change. The surface of a wafer is not perfectly flat. Vertical adjustments are made by the wafer stage, depending on the surface topography of the wafer, to maintain the distance between the last optical element and the exposure area constant. The volume of the space between the wafer and last optical element changes when the wafer is moved up and down. As the volume changes, the pressure and forces of the immersion fluid acting on both the last optical element and the wafer stage also change.

The dynamic forces and pressures acting on the last optical element caused by the motion of the immersion fluid may cause the last optical element to become distorted and/or moved either up or down from its ideal position. As a result, the last optical element may be out of focus, resulting in a poor exposure. Similar forces acting on the wafer stage may affect its performance as well.

At high stage speeds the meniscus can be perturbed to the point where it breaks down, particularly at the leading edge. The breakdown is characterized by the escape and deposition of fluid droplets on the wafer where it emerges from the fluid. Such droplets are undesirable. They can entrap air, creating bubbles, when the wafer passes under the immersed lens on a subsequent scan. Also if the droplets dry on the wafer, any contaminants in the droplet, for example residues dissolved from the resist, remain deposited on the wafer.

A dynamic fluid control system and method capable of compensating for dynamic changes in the forces exerted on the last optical element and stage by the immersion fluid caused by the motion of the immersion fluid and movements of the stage is therefore needed.

SUMMARY

A dynamic fluid control system and method capable of reducing dynamic forces from the fluid on the last optical element and substrate stage, caused by the motion of the immersion fluid, is disclosed. The system includes an imaging element that defines an image and a stage configured to support a substrate. An optical system is provided to project the image defined by the imaging element onto the substrate. The optical system includes a last optical element. A gap filled with immersion fluid is provided between the substrate and the last optical element. A dynamic force control system is provided to maintain a substantially constant force on the last optical element and stage by compensating for dynamic changes of the immersion fluid caused by the motion of the immersion fluid through the gap and/or movement of the stage.

DETAILED DESCRIPTION

Figure 1:
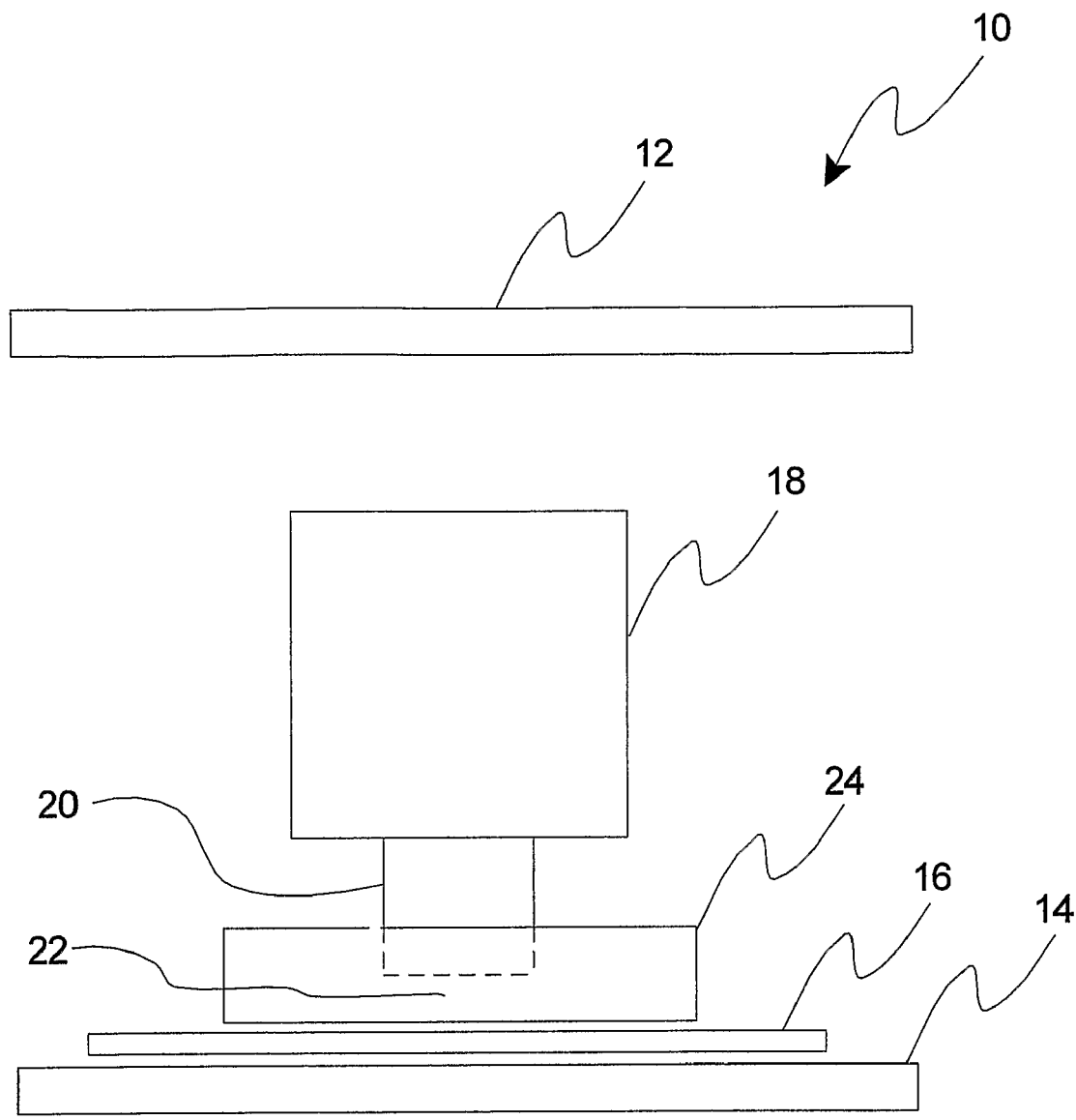
FIG. 1 is a diagram of a lithography machine according to the present invention.

Referring to FIG. 1, an immersion apparatus is shown. The immersion apparatus 10 includes an imaging element 12 which defines an image, a stage 14 configured to support a substrate 16, and an optical system 18 configured to project the image defined by the imaging element 12 onto the substrate 16. The optical system 18 includes a "last" or "final" optical element 20. A gap 22 is provided between the substrate 16 and the last optical element 20. A fluid injection and removal element 24 provides immersion fluid between the substrate 16 and the last optical element 20.

In one embodiment, the imaging element 12 is a reticle or mask. In other embodiments, the imaging element is a programmable micro-mirror array capable of generating the image, such as described in U.S. Pat. Nos. 5,296,891, 5,523, 193, and PCT applications WO 98/38597 and 98/33096, all incorporated herein by reference. In one embodiment, the stage 14 is a fine stage that is supported by a coarse stage (not shown). The fine stage is responsible for fine position adjustment of the substrate 16 in, depending on the design, anywhere from one to six degrees of freedom (x, y, z, θx, θy and θz). Similarly, the coarse stage is responsible for moving the substrate 16 on the fine stage 14 in one to six degrees of freedom. According to various embodiments, the fine stage 14 may be supported on the coarse stage by magnetic levitation, air bellows, pistons, vacuum, or springs, as are all well known in the art. In yet other embodiments, the fluid injection and removal element 24 is a nozzle such as that described in PCT application No. PCT/US04/22915 filed Jul. 16, 2004 entitled "Apparatus and Method for Providing Fluid in Immersion Lithography" or the environmental system described in PCT Application PCT/IB2004/002704 filed Mar. 29, 2004 and entitled "Environmental System Including Vacuum Scavenge For Immersion Lithography Apparatus", both incorporated by reference herein for all purposes.

Figure 2:
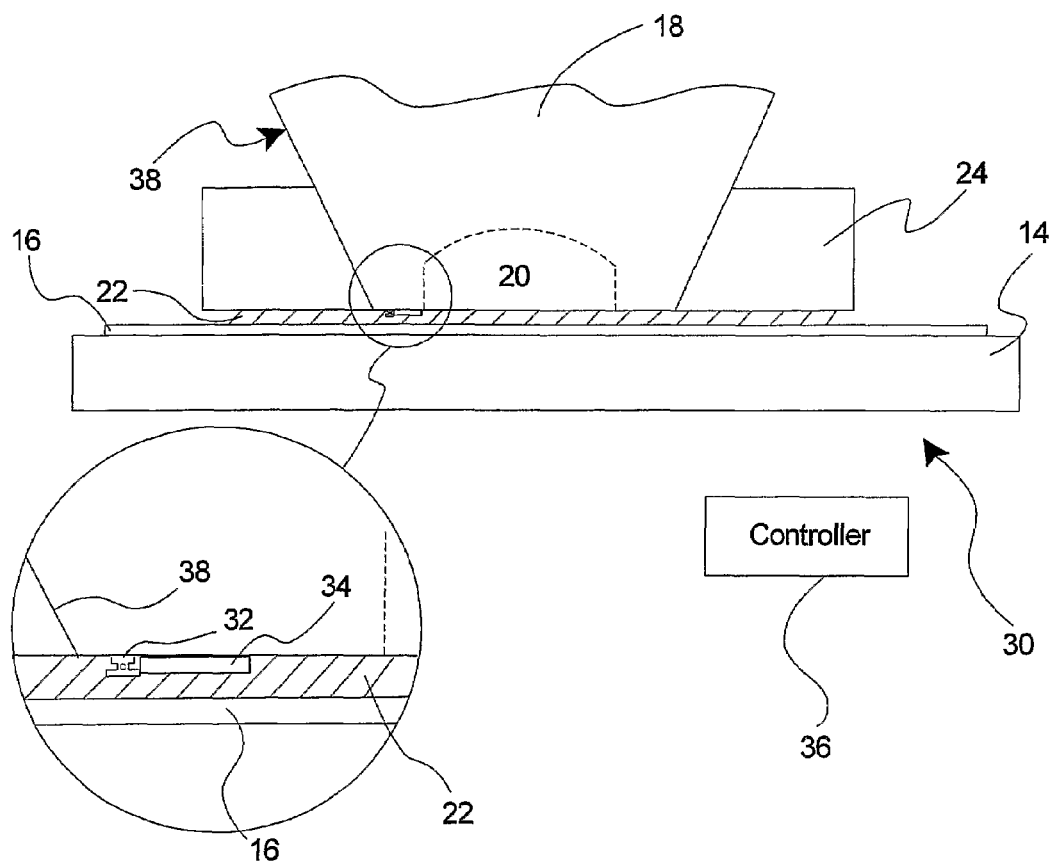
FIG. 2 is a diagram of a dynamic force control system used with the immersion machine of the present invention.

Referring to FIG. 2, a diagram of a dynamic force control system 30 used with the immersion apparatus 10 is shown. The system 30 includes one or more pressure sensors 32 and one or more actuators 34 arranged adjacent to the last optical element 20 (for the sake of simplicity, only a single sensor 32 and actuator 34 pair is shown in FIG. 2). The pressure sensors 32 are positioned adjacent the gap 22 in approximately the same plane as the bottom surface of the last optical element 20. The bottom surface of the last optical element 20 is sometimes referred to as the "boundary" surface of the lens because it bounds or is in contact with the immersion fluid in the gap 22. The last optical element 20 is held in position by a housing 38 of the optical system 18.

The system 30 also includes a control element 36. During operation, the sensors 32 measure pressure changes on the boundary surface of the last optical element 20. The control element 36 generates control signals that control the actuators 34 in response to the measured pressure readings respectively. The actuators 34 create local changes in fluid pressure to compensate for the dynamic pressure changes caused by motion of the immersion fluid. For example, if the fluid pressure increases, the actuators act to relieve the pressure, and vice-versa. In one embodiment, the sensors 32 and actuators 34 are arranged on the housing 38 adjacent to and around the periphery of the boundary surface of the last optical element 20. In another embodiment fluid flow sensors are also used to help define the fluid dynamic state, as described in more detail below.

Figure 3A:
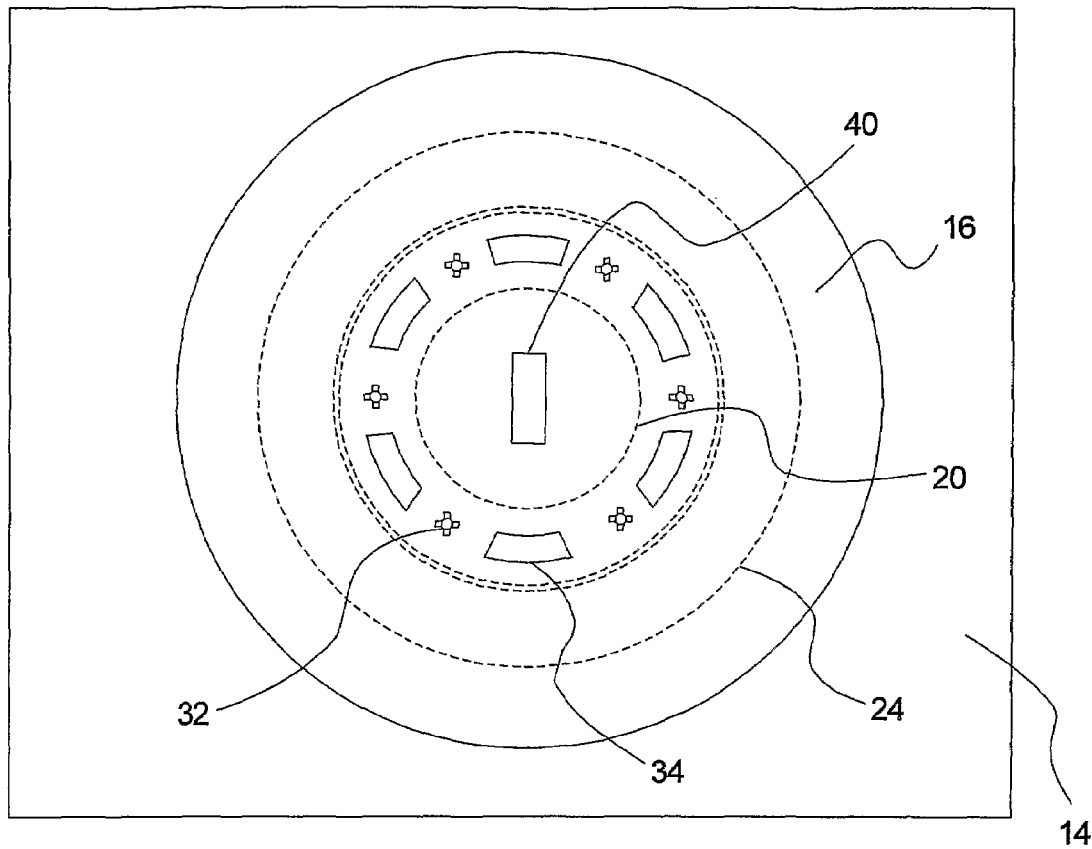
FIG. 3A is a top-down diagram of the sensors and actuators arranged around the last optical element of the dynamic force control system of the present invention.

Referring to FIG. 3A, a top-down view of the sensors 32 and actuators 34 arranged around the last optical element 20 is shown. In the figure, the substrate 16 is shown positioned on the stage 14. The last optical element 20 is positioned over the substrate 16 and defines an imaging field 40. The sensors 32 and the actuators 34 are arranged adjacent to and around the periphery of the last optical element 20. The fluid injection and removal element 24 provides and removes the immersion fluid to and from the gap 22 (not visible in this view) between the substrate 16 and the last optical element 20.

The normal flow of the immersion fluid through the gap 22 creates static forces on the last optical element 20 and stage 14. Changes in the flow rate of the immersion fluid, stage acceleration and motion, vertical adjustments of the wafer, etc., however, may all cause the immersion fluid to create dynamic forces on the last optical element 20 and wafer stage 14. Sensors 32 positioned locally near or under the last optical element 20 monitor the local static and dynamic pressure changes and provide information to the control element 36, so corrective measures can be taken. According to one embodiment, the pressure sensors 32 are positioned in the same horizontal plane as the boundary surface of the last optical element 20. The pressure sensors 32 are oriented such that only the pressure normal to the surface of the boundary surface is measured. Since the immersion fluid is bounded by the horizontal plane defined by the boundary surface, there is no component of momentum in the direction normal to the boundary surface.

Figure 3B:
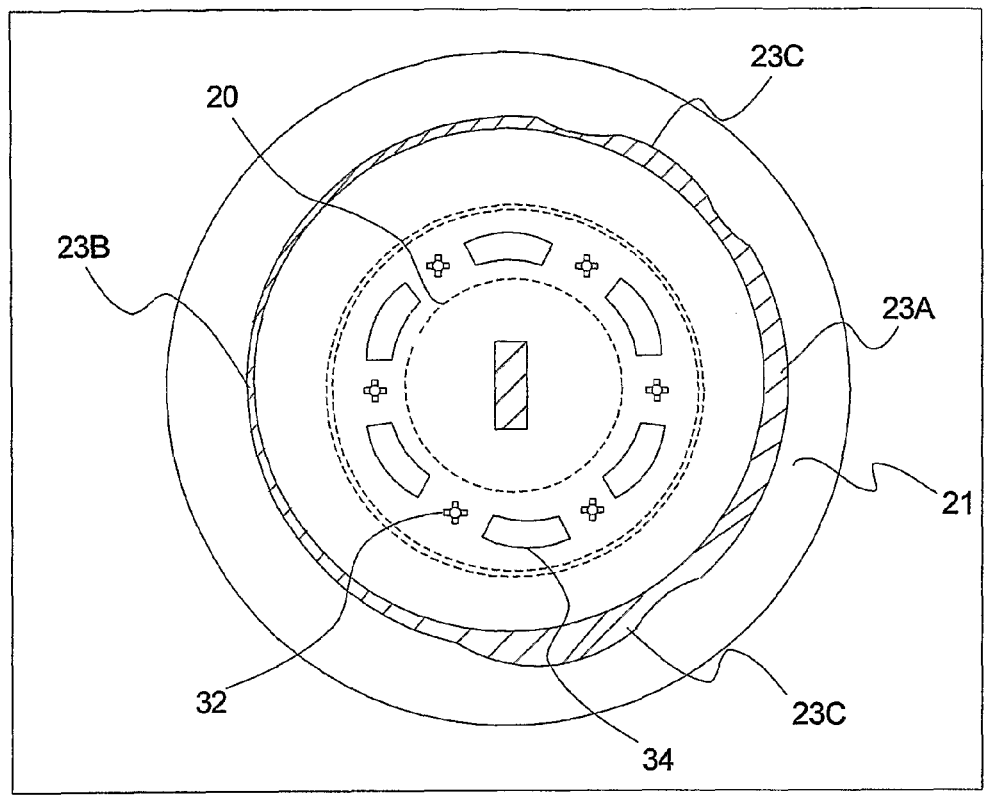
FIG. 3B is a top-down diagram of the dynamic force control system, showing the effects of stage motion on the fluid meniscus.
Figure 3C:
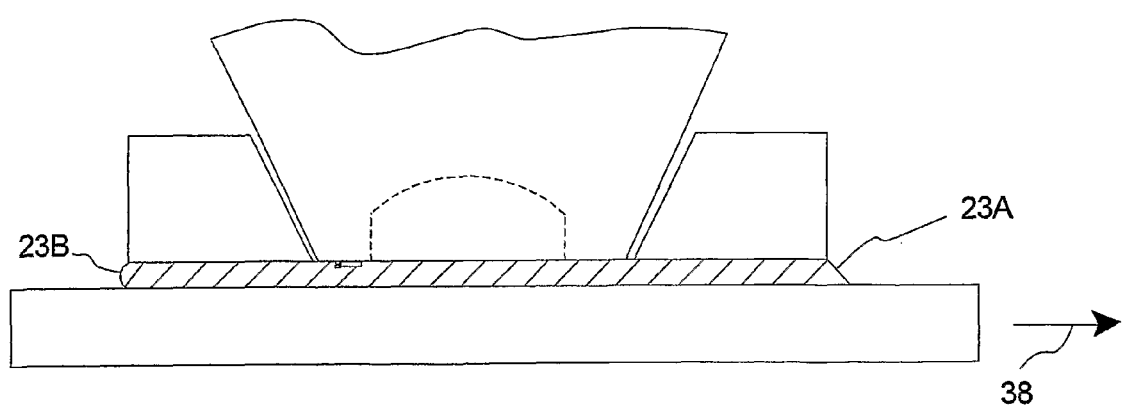
FIG. 3C is a side view diagram of the dynamic force control system, showing the effects of stage motion on the fluid meniscus.

FIGS. 3B and 3C show the effects of stage motion on the fluid meniscus 21. In the figures the stage is moving to the right as designated by arrows 38. This motion causes the shape of the fluid boundary to be different at the leading and trailing edges, as shown at 23a and 23b respectively. Specifically, the meniscus tends to extend outward at the leading edge 23a and pull-in at the trailing edge 23b. This dynamic change of the immersion fluid creates dynamic changes in force on both the stage and the last optical element. In addition, these changes create waves 23c in the fluid which propagate along the meniscus around the lens region. These waves 23c also contribute to the dynamic pressure changes on the last optical element 20 and the wafer stage.

The pressure sensors 32 used with the system 30 may be a manometer, a capacitive manometer, a piezoelectric transducer or any other type of pressure sensor. The actuators 34 may be pistons, diaphragms, bellows, pressure head partial vacuum tubes, or electrocapillary pressure elements, such as described in M. Prins et al, Science 291, 277(2001), incorporated by reference herein for all purposes.

Figure 4:
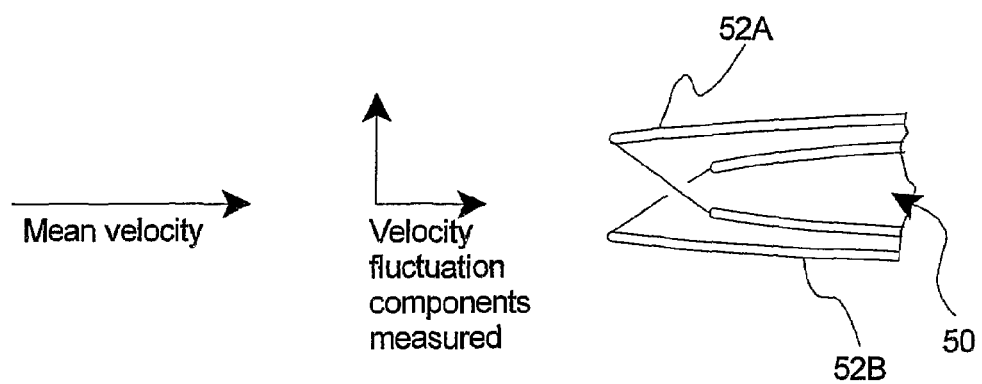
FIG. 4 is a diagram of a sensor used in the dynamic force control system according to one embodiment of the invention.

In other embodiments fluid flow sensors are also used to help define the fluid dynamic state. Referring to FIG. 4, a fluid flow velocity sensor 50 according to one embodiment is shown. The sensor 50 is an "X-type" hot wire sensor that includes two non-contacting wires 52a and 52b of relatively short length that are mounted horizontally and at right angles with the flow direction of the immersion fluid. During operation, the temperature of the two wires 52a and 52b are monitored. From the measured temperature changes, the velocity of the immersion fluid in the normal direction can be monitored. Examples of X-type hot wire sensors are from TSI Inc. of Minneapolis, Minn. From the velocity measurements, in addition to the pressure measurements, the effects of changes in the immersion fluid momentum and transient forces acting on the last optical element and wafer stage can be determined.

Figure 5A:
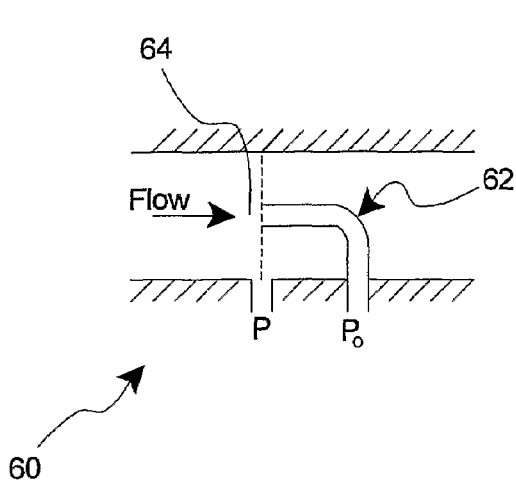
FIGS. 5A and 5B are diagrams of other sensors according to additional embodiments of the invention.

Referring to FIG. 5A, a diagram of another sensor 60 that can be used to measure both fluid pressure and velocity is shown. This sensor 60 includes a total head tube 62 with a wall static pressure tap 64, such as one of the pressure sensors mentioned above, to measure both the stagnation pressure ($p_o$) and the static pressure (p). The stagnation pressure is the pressure measured by a pressure sensor at a point where the fluid is not moving relative to the sensor.

Figure 5B:
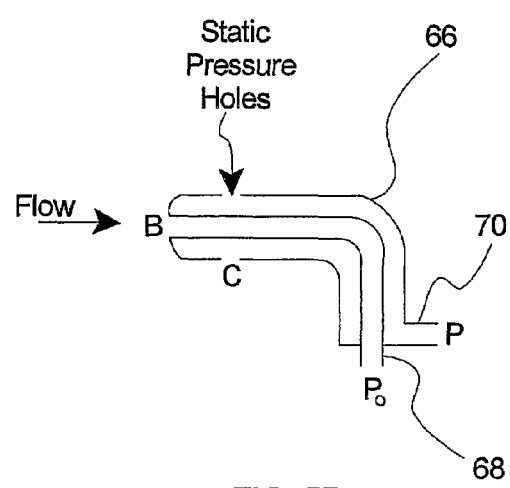

Alternatively, as shown in FIG. 5B, a Pitot tube 66 is used to measure both static and stagnation pressures. The pressure measured at point 68 is the stagnation pressure ($p_o$) since the velocity of the local flow at the entrance of the tube is zero. The pressure (p) at point 70 is different because the local flow velocity is not zero. The velocity of the fluid can then be calculated using Bernoulli's equation and the following assumptions.

$$p_o = p + \tfrac{1}{2}\rho v^2, \quad (1)$$

where $\rho$ is the fluid density. The fluid velocity can then be determined:

$$v = [2(p_o - p)/\rho]^{1/2} \quad (2)$$

Both local fluid flow velocity and pressure are thus determined with this type of sensor.

There are several flow assumptions that restrict the use of Bernoulli's equation:
1. steady flow
2. incompressible flow
3. frictionless flow (low viscosity)
4. flow along a streamline Assumption 2 is assumed to be acceptable, because the flow velocities are much less than the speed of sound in the fluid. With assumption 4, it is assumed that the Pitot tube axis is aligned with the flow direction. Since the fluid, by design, will typically flow along the axis of the scanning stage, assumption 4 is acceptable. Assumption 3 is equivalent to requiring a high Reynolds number (but not too high for laminar flow to be maintained). Assumption 1 however is questionable. Therefore calibration will be required for accurate velocity and pressure determination. The Pitot tube is also limited in frequency response. If higher frequency response is desired, the hot wire velocity sensor may be used instead.

In unsteady flow, where streamline directions are changing, multiple Pitot tube heads, pointing in orthogonal directions, or directions where the flow is known from past measurements to point, may aid in operation of the sensor.

Figure 6:
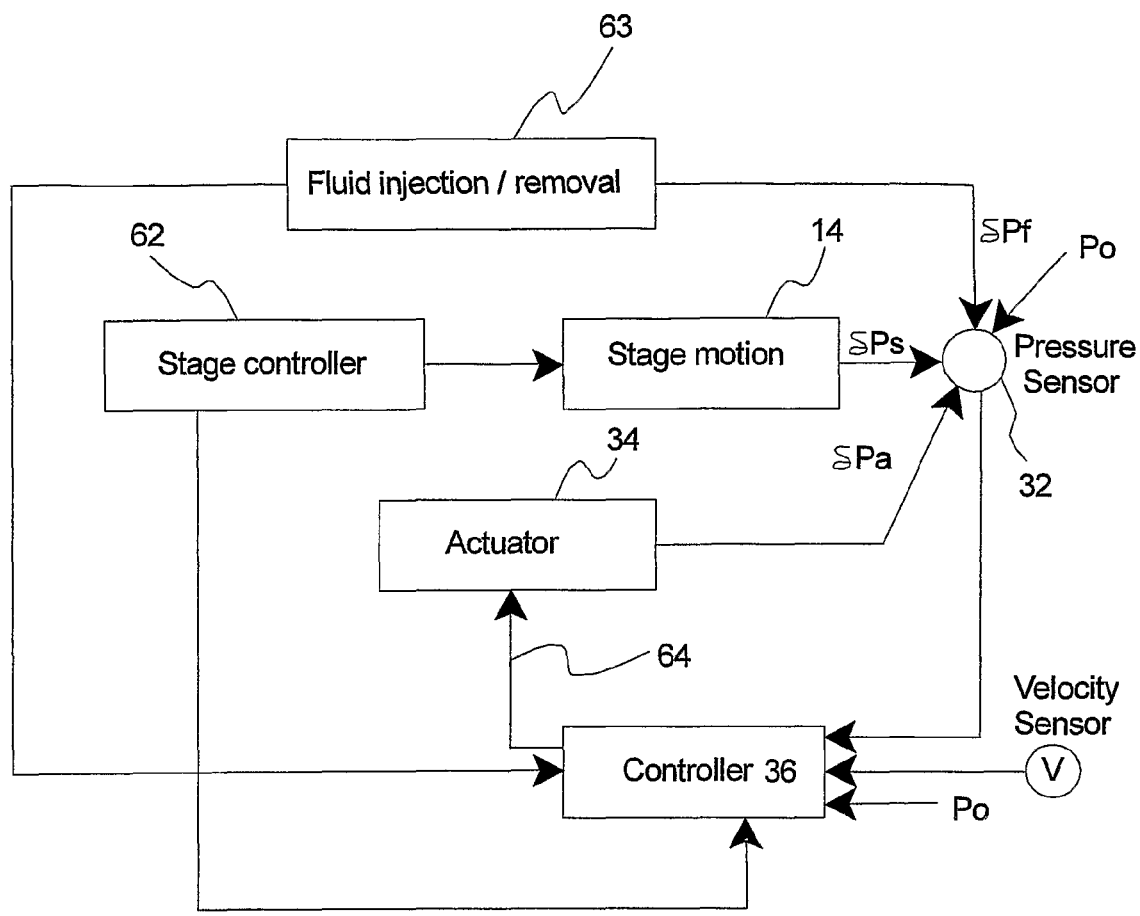
FIG. 6 is a schematic illustrating the operation of the control element according to one embodiment of the present invention.

Referring to FIG. 6, a schematic illustrating the operation of the control element 36 is shown. For clarity, only a single pressure sensor 32 (such as the pressure and/or velocity sensors of FIGS. 3A, 5A or 5B), and actuator 34 are used. The pressure sensor 32 generates a pressure control signal to the controller 36 that is indicative of the following: (i) the stage controller 62 directing the stage 14 to move in the horizontal and/or vertical directions, the resulting stage motion causing pressure change $\delta Ps$ at the pressure sensor 32; (ii) operation of the fluid injection/removal system 63 may cause an additional pressure change $\delta Pf$ at the pressure sensor; (iii) simultaneous operation of the actuator 34 causes an additional pressure change $\delta Pa$; and (iv) the static pressure $P_0$ as measured by the sensor 32. The total pressure as measured at the sensor 32 is therefore $P_0 + \delta Ps + \delta Pf + \delta Pa$. Using an algorithm, the controller 36 uses information from the pressure sensor 32, along with information from the stage controller to generate a control signal 64 to the actuator 34. The actuator's response to the signal 64 is a pressure change $\delta Pa$ at the pressure sensor 32 which substantially cancels the pressure changes from the stage motion and fluid injection/removal system as specified by equation (3) below:

$$\delta Pa = -(\delta Ps + \delta Pf). \quad (3)$$

Thus the effect of dynamic pressure changes on both the last optical element 22 and the wafer stage are minimized. In other embodiments signals from the velocity sensor or the stage controller may be absent, or information from the fluid injection/removal system may be provided to the controller.

In reducing the pressure fluctuations affecting the last lens element and wafer stage, the controller 36 is likely to also reduce somewhat the amplitudes of the waves 23c. This in turn may improve the performance of the fluid injection/removal system. It may also reduce the chances of breakdown of the leading edge meniscus and thus avoid the formation of isolated fluid droplets on the wafer.

The above description is appropriate for a linear system, where the pressure change $\delta Ps$ created by the stage motion is independent of the pressure change $\delta Pf$ created by the fluid injection/removal system, and the pressure change $\delta Pa$ from the actuator. In reality, the fluid motion may make the system response non-linear, so that $\delta Ps$, $\delta Pf$ and $\delta Pa$ are functions of one another. However Eq. 3 remains valid. Also, if the pressure changes are small enough, the system response may be approximated as linear.

Satisfying Eq. 3 is complicated by the fact that the controller can't respond instantaneously to the pressure sensor signal, nor can the separate contributions to the pressure sensor signal, δPs, δPf, δPa, be measured. Additionally, since fluid is moving, the rate of change of the pressures will be important as well. The controller therefore needs an algorithm to use information from the stage and fluid injection/removal systems, as well as the total pressure signal, over a period of time to estimate the appropriate signal to send to the pressure actuator. The algorithm may be obtained in a number of ways:

1. A fluid dynamic model may be constructed of the fluid cell and the fluid dynamic forces associated with stage motion and fluid injection or removal calculated. Pressure changes at the pressure sensor resulting from these effects are then calculated, resulting in an estimate of the required pressure actuator signal. The model may have some adjustable parameters, whose setting will minimize the total pressure change at the pressure sensor, Eq. 3.

Figure 9:
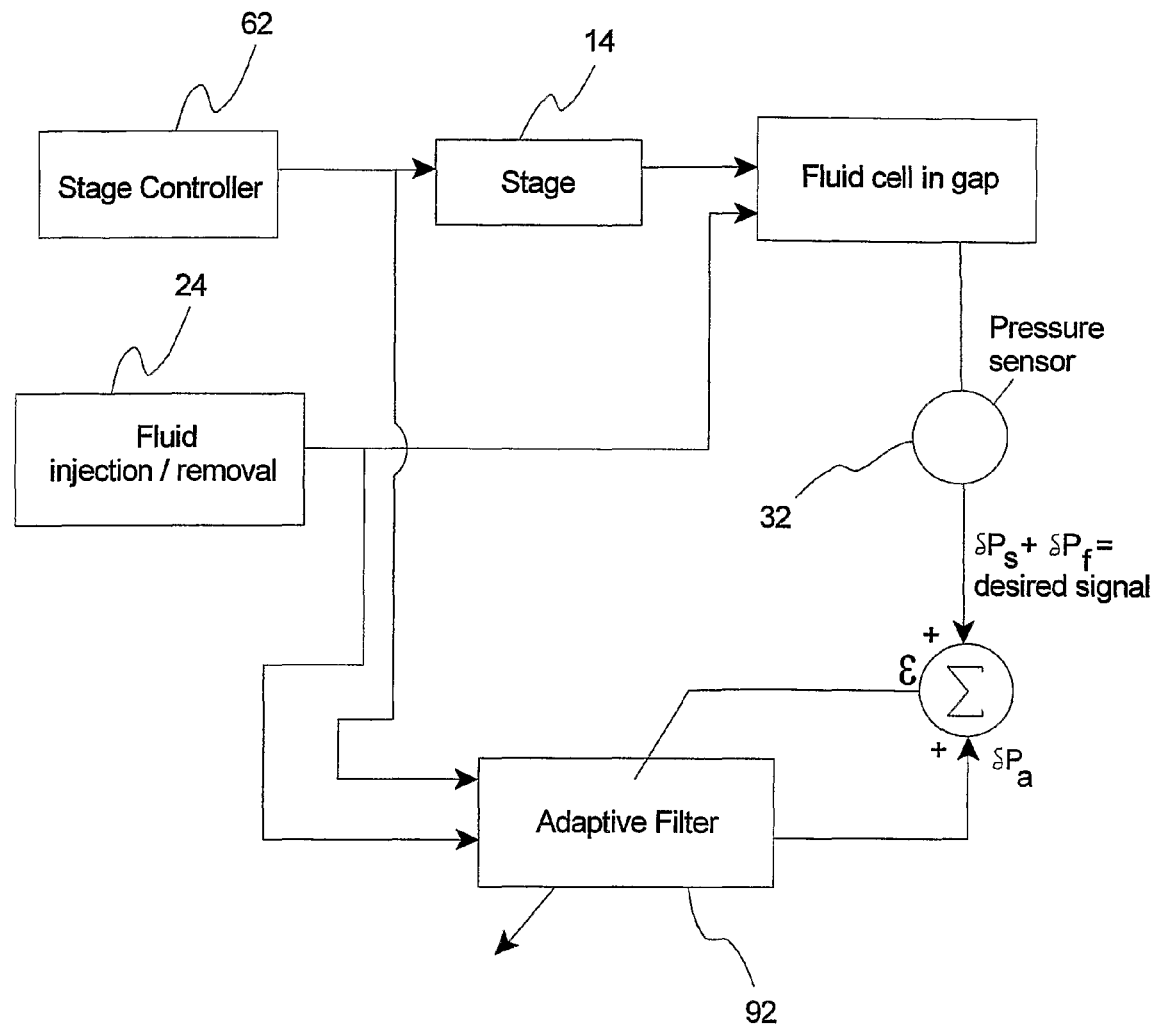
FIG. 9 is a schematic illustrating the determination of a control algorithm for fluid pressure control.

2. The algorithm may be established empirically, using an adaptive filter to create a model of the fluid cell and its response to stage and fluid injection/removal perturbations. FIG. 9 illustrates such a filter and its training process. An adaptive filter is a linear filter with adjustable weights which are altered to make the output signal agree with a desired signal. In FIG. 9 signals from the stage 14 and fluid injection/removal element 24 also go to the adaptive filter as inputs. The output of the adaptive filter 92 is an estimate of the pressure at the pressure sensor 32 caused by the actuator. The relation between the actuator signal and the pressure at the sensor 32 is established in an earlier calibration, in the absence of perturbations from the stage and fluid injection/removal systems. In FIG. 9 the desired signal is the signal from the pressure sensor 32 caused by perturbations from the stage 14 and fluid of the injection/removal element 24. The error signal ϵ between the pressure sensor signal and the pressure sensor signal predicted by the adaptive filter 92 is fed back to the filter and the weights adjusted to minimize ϵ. Note that the polarities of the summing junction lead to the relation ϵ=δPs+δPf+δPa. Thus if the weights can be successfully adjusted to make ϵ negligibly small, we have established the condition of Eq. 3.

After successfully training the adaptive filter 92, the controller 36 containing the adaptive filter is connected to the system as in FIG. 6.

3. Adaptive filters are most appropriate for systems which are linear or only weakly non-linear. If the fluid dynamics of the fluid cell couple the pressure changes caused by the stage and fluid injection/removal systems and the actuator together too strongly, the adaptive filter may be replaced with a neural network system, which can represent non-linear relations. The neural network is trained and utilized essentially the same way as the adaptive filter.

If the environmental conditions of the fluid cell change, the optimal parameters of the controller algorithm may change as well. The controller may include an adaptive feature which allows it to continue to train the algorithm, as environmental conditions change. Thus, if the algorithm is based on a fluid dynamic model, certain adjustable parameters in the model may be changed to minimize the total pressure change at the pressure sensor. If the algorithm is an adaptive filter or a neural network, the adjustable weights may be changed to minimize the total pressure change at the pressure sensor.

Figure 7:
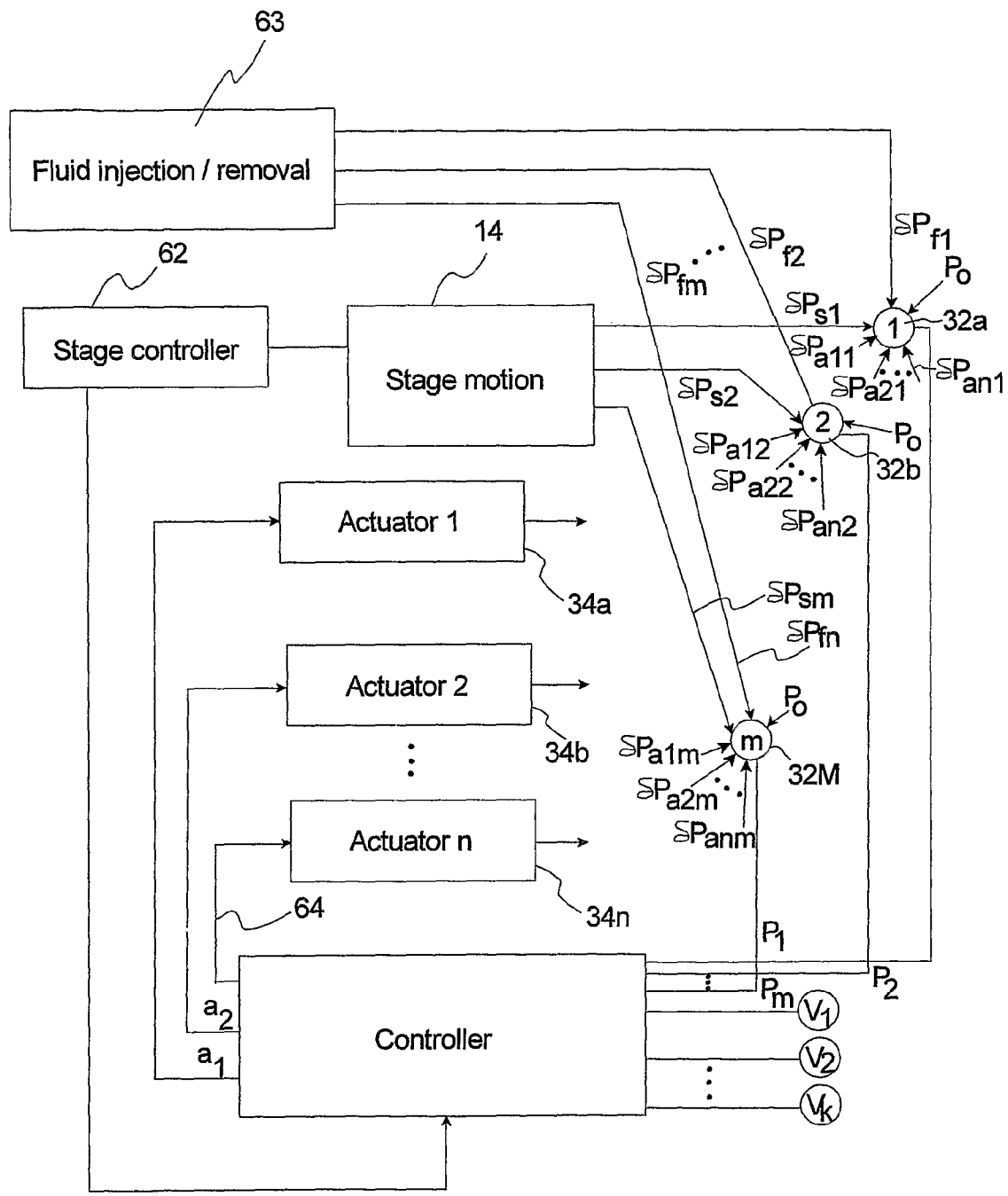
FIG. 7 is another schematic illustrating operation of the control element according to another embodiment of the present invention.

Referring to FIG. 7, another schematic illustrating operation of the control element 36 coupled to multiple pressure and/or flow velocity sensors 32 and multiple actuators 34 is shown. In FIG. 3A, the number of actuators was equal to the number of pressure and velocity sensors. In alternative embodiments, however, the number of actuators 34, pressure sensors 32, and/or flow velocity sensors may be different. In FIG. 7 there are n actuators 34a-34n, m pressure sensors 32a-32m, and k flow velocity sensors V1-Vk. Each sensor 32a-32m generates a pressure signal P1-Pm derived from the four pressure components (i) through (iv) as discussed above. Each actuator 34a-34n creates a pressure change at each of the pressure sensors 32a-32m, so that the measured δPa at each pressure sensor is the accumulation of the pressure changes caused by all the actuators 34a-34n. More specifically, actuator i generates a pressure change δPaij at pressure sensor j. The total pressure change at sensor j from all the n actuators is given by $\Sigma_{i=1,n} \delta Paij$. The controller 36 processes the m pressure sensor signals, the k flow velocity sensor signals, and information from the stage controller and fluid injection/removal system, and generates actuator signals a1-an to the actuators 34a-34n, so that the actuator pressures at the pressure sensors satisfy the relations:

$$\Sigma_{i=1,n} \delta Paij = -(\delta Psj + \delta Pfj), \text{ for } j=1,m. \quad (4)$$

This insures that the effects of dynamic pressure changes on both the last optical element and the wafer stage are minimized. In other words, controlling the actuators 34a-34n enables the dynamic net forces and net moments (i.e., torque) acting on the final optical element 20 and stage caused by the dynamics of the immersion fluid to be minimized. When the stage is moving, the contact angle of the immersion fluid is different at the leading edge versus the trailing edge. This creates different forces acting on the leading edge and trailing edges of housing 38 and the last optical element 20. These different forces may create net moments or torques on the last optical element or wafer stage, which can be corrected using the aforementioned equation.

In one embodiment, as illustrated in FIG. 3B, the plurality of sensors 32 and actuators 34 are arranged around the periphery of the last optical element 20. With this arrangement, the waves 23c created at the meniscus of the immersion fluid are controlled, and breakdown of the leading edge meniscus during stage motion is avoided or minimized. In other embodiments, the sensors 32 and actuators 34 can be arranged at different locations adjacent the last optical element 20.

Designing an algorithm to satisfy Eqs. 4 is analogous to the description above in connection with FIG. 6 and Eq. 3.

Throughout this discussion, the terms force and pressure have been used interchangeably. It should be noted, however, that technically, the two terms are slightly different. Pressure is a measure of force per unit area. Many of the sensors that are commercially available are designed to measure pressure. Sensors, however, could be calibrated to measure force and could be used with the present invention.

In normal operation the actuator signals will typically lie within a limited range of values, which are determined by the limited range of fluid perturbations allowed by the controller 36. However if the fluid system is strongly perturbed, some actuator signals may fall outside the above range. For example, if the fluid injection fails to completely fill the gap 22, leaving an air void under the part of the last optical element, the actuator signals predicted by the controller 36 are likely to differ substantially from their normal values. Or if the leading edge meniscus breaks down, leaving isolated droplets on the wafer, air may be drawn into the gap 22, and the actuator values predicted by the controller 36 may depart from normal values. It may not be possible for the controller to recover from such pathological conditions, but the aberrant actuator signals can serve as a message to the lithography tool controller that proper immersion conditions in the gap 22 have been lost, and lithographic exposure must be halted until the condition is corrected.

Figure 8A:
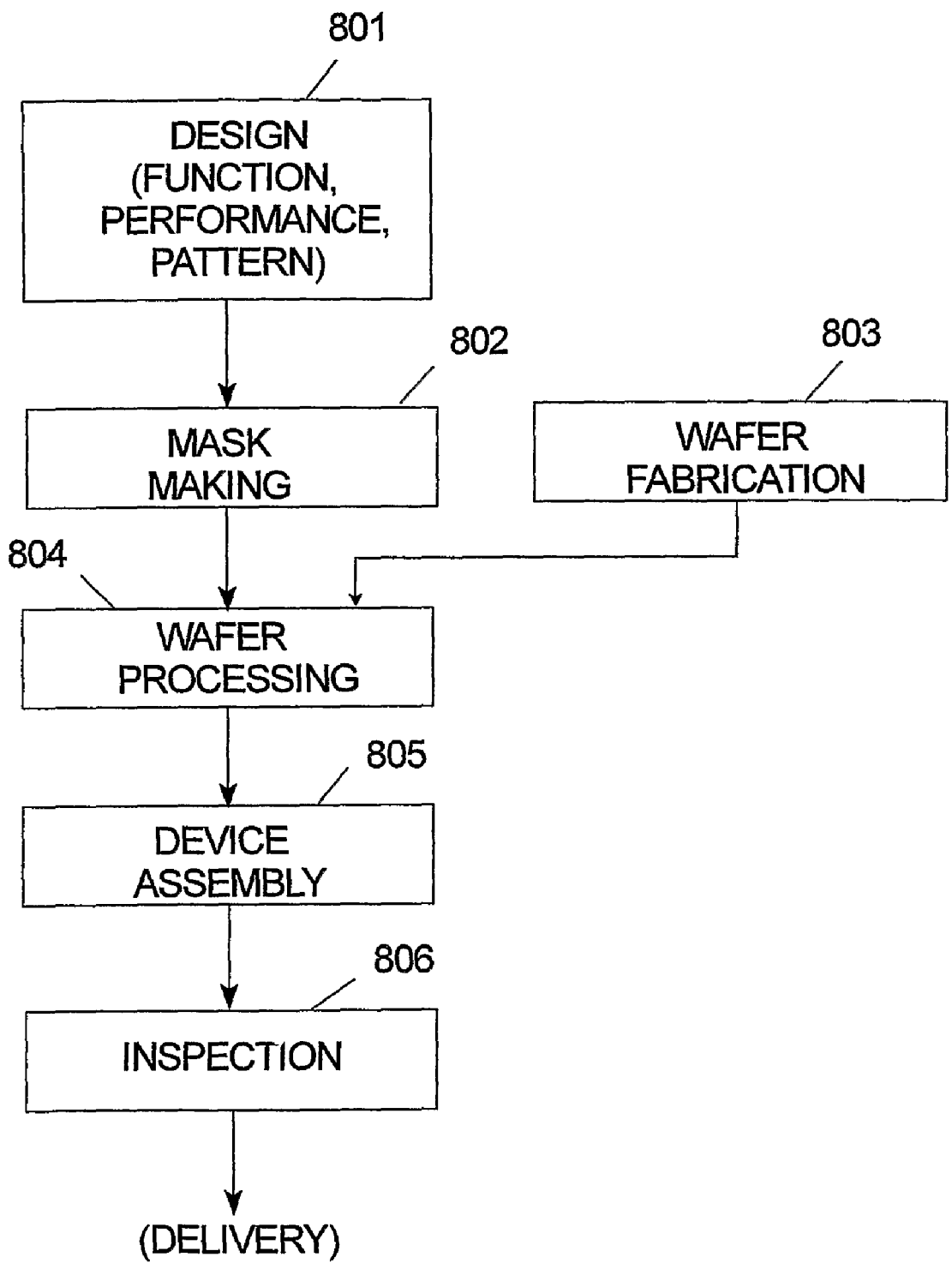
FIGS. 8A and 8B are flow diagrams illustrating the sequence of fabricating semiconductor wafers according to the present invention.

Semiconductor devices can be fabricated using the above described systems, by the process shown generally in FIG. 8A. In step 801 the device's function and performance characteristics are designed. Next, in step 802, a mask (reticle) having a pattern is designed according to the previous designing step, and in a parallel step 803 a wafer is made from a silicon material. The mask pattern designed in step 802 is exposed onto the wafer from step 803 in step 804 by a photolithography system described hereinabove in accordance with the present invention. In step 805 the semiconductor device is assembled (including the dicing process, bonding process and packaging process), finally, the device is then inspected in step 806.

Figure 8B:
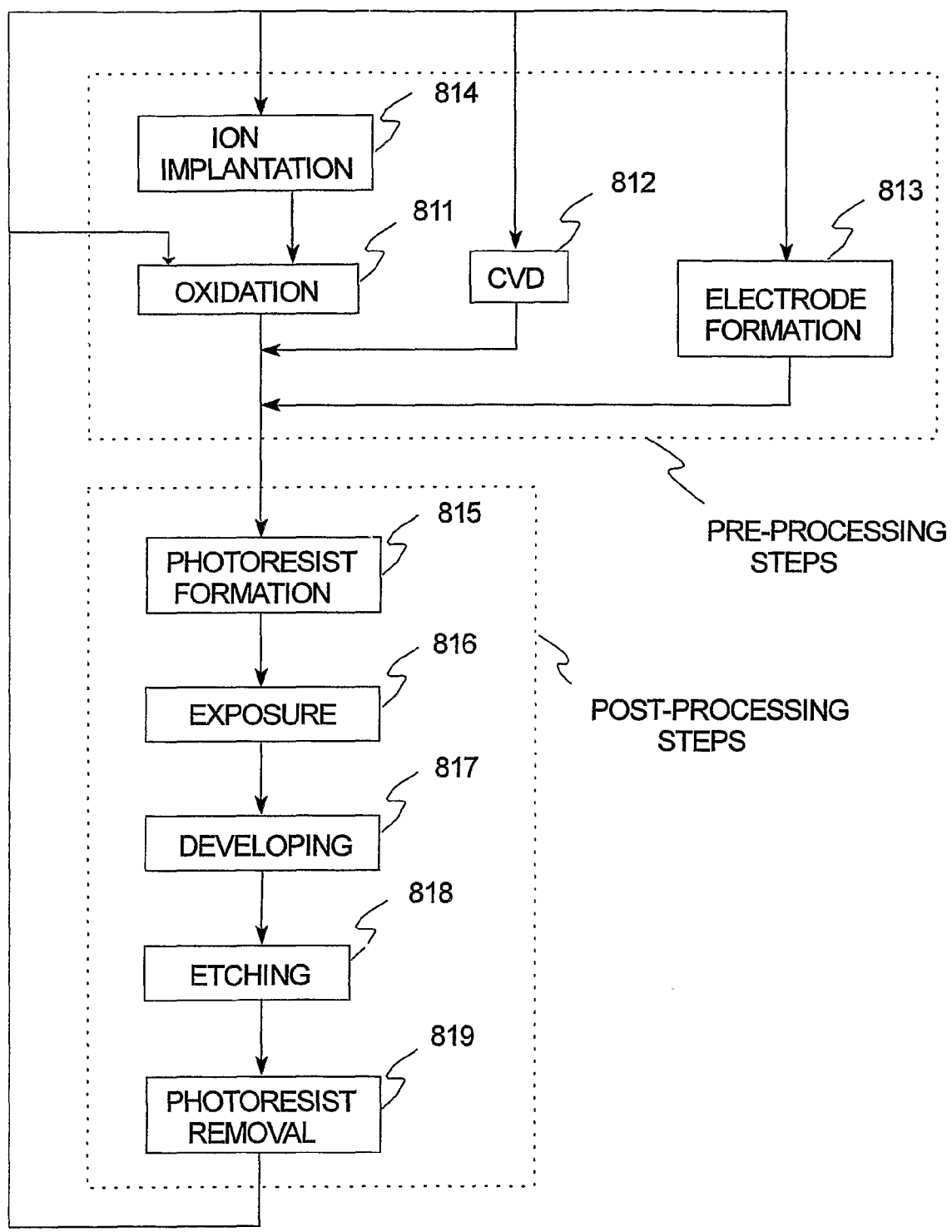

FIG. 8B illustrates a detailed flowchart example of the above-mentioned step 804 in the case of fabricating semiconductor devices. FIG. 8B, in step 811 (oxidation step), the wafer surface is oxidized. In step 812 (CVD step), an insulation film is formed on the wafer surface. In step 813 (electrode formation step), electrodes are formed on the wafer by vapor deposition. In step 814 (ion implantation step), ions are implanted in the wafer. The above mentioned steps 811-814 form the preprocessing steps for wafers during wafer processing, and selection is made at each step according to processing requirements.

It should be noted that the particular embodiments described herein are merely illustrative and should not be construed as limiting. For example, the substrate described herein does not necessarily have to be a semiconductor wafer. It could also be a flat panel used for making flat panel displays. Rather, the true scope of the invention is determined by the scope of the accompanying claims.

What is claimed is:

1. An apparatus, comprising:
a stage that supports a substrate;
an optical system that projects an image onto the substrate, the optical system having a last optical element that is spaced from the substrate by a gap at least partly filled with an immersion liquid; and
a dynamic force control system that maintains a substantially constant force on the last optical element and the stage by locally changing the immersion liquid pressure in the gap to compensate for dynamic changes of the immersion liquid caused by motion of the immersion liquid through the gap and/or movement of the stage.

2. The apparatus of claim 1, wherein the dynamic force control system further comprises a sensor positioned adjacent the last optical element.

3. The apparatus of claim 2, wherein the sensor is positioned in the gap adjacent the last optical element.

4. The apparatus of claim 2, wherein the last optical element defines a boundary surface that bounds the immersion liquid in the gap, the sensor positioned in the same plane as the boundary surface.

5. The apparatus of claim 2, wherein the sensor is at least one pressure sensor.

6. The apparatus of claim 5, wherein the last optical element has a boundary surface that bounds the immersion liquid in the gap, the pressure sensor measures pressure changes substantially normal to the boundary surface caused by motion of the immersion liquid in the gap.

7. The apparatus of claim 2, wherein the sensor comprises one from the following group of sensors: a manometer, a capacitance manometer, or a piezoelectric transducer.

8. The apparatus of claim 2, wherein the sensor is at least one fluid flow velocity sensor.

9. The apparatus of claim 8, wherein the fluid flow velocity sensor comprises two wires that measure the velocity of the immersion liquid in a direction normal to the surface of the last optical element by measuring the temperature of the two wires.

10. The apparatus of claim 8, wherein the fluid flow velocity sensor comprises a lead tube with a wall static tap.

11. The apparatus of claim 8, wherein the fluid flow velocity sensor comprises a Pitot lead tube with static pressure holes.

12. The apparatus of claim 2, wherein the sensor measures static pressure changes created by the immersion liquid.

13. The apparatus of claim 2, wherein the sensor measures dynamic pressure changes created by the immersion liquid.

14. The apparatus of claim 1, further comprising a plurality of sensors each positioned adjacent the last optical element.

15. The apparatus of claim 1, wherein the dynamic force control system further comprises an actuator that locally changes the immersion liquid pressure in the gap to compensate for changes in the force exerted on the last optical element and stage caused by motion of the immersion liquid through the gap and/or motion of the stage.

16. The apparatus of claim 15, wherein the actuator comprises one from the following group of actuators: pistons, diaphragms, bellows, pressure head partial vacuum tubes, or electrocapillary pressure elements.

17. The apparatus of claim 1, wherein the dynamic force control system further comprises a plurality of actuators each arranged at different locations adjacent a surface of the last optical element in contact with the immersion liquid.

18. The apparatus of claim 1, wherein the dynamic force control system further comprises:
a sensor positioned adjacent a surface of the last optical element in contact with the immersion liquid;
an actuator located adjacent the last optical element, the actuator compensates for dynamic forces exerted on the last optical element and the stage; and
a controller that controls the actuator in response to the sensor to compensate for the dynamic forces exerted on the last optical element and the stage caused by motion of the immersion liquid through the gap and/or motion of the stage as measured by the sensor.

19. The apparatus of claim 18, wherein the controller uses an adaptive filter algorithm to control the actuator.

20. The apparatus of claim 18, wherein the sensor generates a pressure signal indicative of one or more of the following components: (i) sensed pressure changes exerted by the immersion liquid caused by movements of the stage; (ii) sensed pressure changes exerted by the immersion liquid caused by injection and removal of the immersion liquid; (iii) sensed pressure changes exerted by the immersion liquid caused by the actuator; and (iv) sensed static pressure exerted by the immersion liquid.

21. The apparatus of claim 20, wherein the controller generates a control signal to control the actuator in response to the pressure signal from the sensor and a fluid velocity signal.

22. The apparatus of claim 18, wherein the controller generates a control signal to control the actuator, the control signal being generated from an algorithm that uses information from one or more of the following: (i) movement of the stage; (ii) a liquid injection and removal element that injects and removes immersion liquid from the gap; (iii) a pressure signal as measured by the sensor.

23. The apparatus of claim 22, wherein the controller further uses the algorithm to predict the control signal as learned over a period of time.

24. The apparatus of claim 23, wherein the algorithm uses an adaptive filter to create a model of the behavior of the immersion liquid in response to the motion of the stage and liquid injection and removal.

25. The apparatus of claim 23, wherein the algorithm uses a mathematical model that models the behavior of the immersion liquid in response to the motion of the stage and the liquid injection and removal to predict the control signal.

26. The apparatus of claim 23, wherein the algorithm uses a neural network that models the behavior of the immersion liquid in response to the motion of the stage and the liquid injection and removal to predict the control signal.

27. The apparatus of claim 23, wherein the algorithm further includes an adaptive feature which adapts the algorithm to compensate for environmental conditions changing at the sensor.

28. The apparatus of claim 1, wherein the dynamic force control system further comprises:

a plurality of actuators arranged adjacent the last optical element and in contact with the immersion liquid, the plurality of actuators compensate for dynamic changes of the force exerted by the immersion liquid caused by motion of the immersion liquid through the gap and/or motion of the stage;

a plurality of velocity sensors that measure the velocity of the immersion liquid;

a plurality of sensors arranged adjacent the last optical element and in contact with the immersion liquid; each of the plurality of sensors generates a pressure signal indicative of the following components: (i) sensed pressure changes exerted by the immersion liquid caused by movements of the stage; (ii) sensed pressure changes exerted by the immersion liquid caused by injection and removal of the immersion liquid; (iii) sensed pressure changes exerted by the immersion liquid caused by each of the plurality of actuators; and (iv) sensed static pressure exerted by the immersion liquid; and a controller that generates a plurality of control signals to the plurality of actuators respectively, the controller generating the plurality of control signals in response to the plurality of pressure signals from the plurality of sensors respectively.

29. The apparatus of claim 28, wherein the plurality of sensors and the plurality of actuators are arranged around the periphery of the last optical element of the optical system.

* * * * *